US011788041B2

(12) United States Patent
Thai (10) Patent No.: US 11,788,041 B2
(45) Date of Patent: Oct. 17, 2023

(54) VENTURI BUBBLE LIGHTING (71) Applicant: SEA VOLUTE, LLC, Gainesville, VA (US)

(72) Inventor: Ari Thai, Fairfax, VA (US)

(73) Assignee: SEA VOLUTE, LLC, Gainesville, VA (US)

(*) Notice: Subject to any disclaimer, the term of this patent is extended or adjusted under 35 U.S.C. 154(b) by 300 days.

(21) Appl. No.: 16/216,728

(22) Filed: Dec. 11, 2018

(65) Prior Publication Data
US 2019/0218489 A1 Jul. 18, 2019

Related U.S. Application Data (60) Provisional application No. 62/597,332, filed on Dec. 11, 2017.

(51) Int. Cl.
C12M 1/00 (2006.01)
A01G 33/00 (2006.01)
C02F 3/12 (2023.01)
C02F 3/20 (2023.01)
A01G 7/04 (2006.01)
C12N 1/12 (2006.01)
C02F 103/20 (2006.01)

(52) U.S. Cl.
CPC ............ C12M 21/02 (2013.01); A01G 7/045 (2013.01); A01G 33/00 (2013.01); C02F 3/1294 (2013.01); C02F 3/202 (2013.01); C12M 29/06 (2013.01); C12M 31/02 (2013.01); C12M 31/08 (2013.01); C12N 1/12 (2013.01); C02F 2103/20 (2013.01)

(58) Field of Classification Search
CPC ...... C12M 21/02; C12M 29/06; C12M 31/02; C12M 31/08; A01G 7/045; A01G 33/00; C02F 3/1294; C02F 3/202; C02F 2103/20; C12N 1/12
USPC ...................................................... 435/296.1
See application file for complete search history.

(56) References Cited

U.S. PATENT DOCUMENTS 5,728,293 A 3/1998 Guoli et al.
6,837,991 B1 1/2005 Norris
(Continued)

FOREIGN PATENT DOCUMENTS

GB 2469198 10/2010
WO WO 2014/201298 12/2014
WO WO 2016/123077 8/2016

OTHER PUBLICATIONS

International Search Report for PCT/US2016/014870, dated May 2, 2016, 2 pages.
(Continued)

Primary Examiner — Michael L Hobbs
Assistant Examiner — Lenora A Abel
(74) Attorney, Agent, or Firm — Nixon & Vanderhye, P.C.

(57) ABSTRACT

A water filtering system includes providing light deep into a liquid used in applications such as the cultivation of both attached and suspended photosynthetic organisms. The system is configured to inject a stream of bubbles into the liquid and a light source is configured to shines light through the bubbles. The bubbles allow some light to travel deep into the liquid along the length of the bubble stream and scatter/deflect some light out of the bubble stream and into the surrounding liquid including screens for growing algae.

20 Claims, 8 Drawing Sheets

(56) References Cited

U.S. PATENT DOCUMENTS

| | | | |
|---|---|---|---|
| 7,578,933 B1 | 8/2009 | Selman | |
| 8,017,366 B1 | 9/2011 | Schuh et al. | |
| 8,262,776 B2 | 9/2012 | Hazlebeck et al. | |
| 8,940,531 B2 * | 1/2015 | Seong | C12M 47/02 |
| | | | 435/292.1 |
| 9,003,695 B2 * | 4/2015 | Oyler | C12N 1/12 |
| | | | 47/1.4 |
| 9,005,918 B2 * | 4/2015 | Dvorak | C12M 27/20 |
| | | | 435/41 |
| 9,040,283 B2 | 5/2015 | Muller-Feuga | |
| 9,045,724 B2 * | 6/2015 | Roux Dit Buisson | |
| | | | C12M 31/12 |
| 9,051,539 B2 | 6/2015 | Snyder et al. | |
| 9,057,043 B2 | 6/2015 | Flynn et al. | |
| 9,102,923 B2 * | 8/2015 | Meiser | C12M 25/06 |
| 9,115,008 B2 † | 8/2015 | Farrish | |
| 9,145,539 B2 | 9/2015 | Turner et al. | |
| 9,388,372 B2 | 7/2016 | Wilson | |
| 2005/0255584 A1 * | 11/2005 | Broneske | C12M 21/02 |
| | | | 435/293.1 |
| 2009/0047722 A1 * | 2/2009 | Wilkerson | C12M 31/10 |
| | | | 435/257.1 |
| 2012/0129245 A1 * | 5/2012 | Neeb | C12M 41/18 |
| | | | 362/249.02 |
| 2013/0233779 A1 * | 9/2013 | Farrish | A01K 63/045 |
| | | | 210/150 |
| 2014/0030801 A1 | 1/2014 | Neeb | |
| 2015/0034539 A1 * | 2/2015 | Farrish | A01G 33/00 |
| | | | 210/150 |

OTHER PUBLICATIONS

Written Opinion of the ISA for PCT/US2016/014870, dated May 2, 2016, 7 pages.

"Inflow Algae Scrubber", *CDMills Designs*, http://cdmillsdesigns.blogspot.com/2013/01/latest-update-on-my-jas-11-design.html, 4 pages.

"The Turbo L4 Algae Scrubber (obsolete)", *Algae Scrubbing*, https://www.algaescrubbing.com/threads/the-turbo-14-algae-scrubber-obsolete.41/, Nov. 2012, 14 pages.

"HOG.5 Hang-On-Glass UAS Upflow Algae Scrubber—1/2 Cube feeding per day", *Santa Monica Filtration*, http://www.santa-monica.cc/HOG5-Hang-On-Glass-UAS-Upflow-Algae-Scrubber—12-Cube-feeding-per-day_p_21.html, 6 pages.

"Venturi effect", definition of Venturi effect by Medical Dictionary, https://medical-dictionary.thefreedictionary.com/Venturi+effect, 2 pages.

* cited by examiner
† cited by third party

VENTURI BUBBLE LIGHTING

CLAIM OF PRIORITY

The present application claims priority to U.S. Provisional Application No. 62/597,332, titled "VENTURI BUBBLE LIGHTING," filed on Dec. 11, 2017, the entirety of which is incorporated by reference herein.

CROSS-REFERENCE TO RELATED APPLICATION

The present application is related to the following commonly-assigned U.S. patent application Ser. No. 15/546,176, title "ALGAE SCRUBBER WITH DIRECTED WATER FLOW," filed Jul. 25, 2017, the entirety of which is incorporated by reference herein.

FIELD OF THE INVENTION

The technology disclosed in this application relates to filtration systems for growing algae in an aqueous solution, and more particularly to system(s) and/or method(s) for providing light for growing algae in an aqueous solution.

INCORPORATION BY REFERENCE

All publications, patent applications, and patents mentioned herein are hereby incorporated by reference in their entirety as if each individual publication or patent was specifically and individually indicated to be incorporated by reference. In case of conflict, the present application, including any definitions herein, will control.

BACKGROUND

In some existing systems for cultivating greenwater (algae suspended in water) such as open pond systems and bioreactors, sunlight is used as a light source for algae growth. These systems are not very efficient as sunlight can only penetrate a short distance into the water. An artificial light source from out of the water has a similar limitation.

In some other bioreactor systems (such as the one described in the patent application US20140030801 A1), the light source is protected in a transparent housing and submerged in water. Even in these systems, light still cannot travel far from the light source. Therefore, multiple submerged light sources might be required to distribute light uniformly throughout the body of water. This leads to the issue of having too much excess heat from the light source being transferred to the water, which might be undesired in certain applications.

In some modern bioreactors (such as the one described in the patent US9388372 B2), a sophisticated device is used to transfer the heat from the LEDs out of the water to dissipate into the ambient air. However, such a device is costly to construct.

In some other applications such as water filtering for home aquaria, algae is grown on a surface submerged in clear water. In such systems, even though light can travel far in the clear water, submerged light sources are still preferred over external light sources to distribute light uniformly over all the grow surface. Therefore, the excess heat issue is also present.

Another disadvantage of the submerged light sources is that they occupy space in the liquid and might limit the flexibility in the design of the bioreactor. For example, FIG. 11 in patent application WO2016123077 A1 describes a bioreactor having a light core in the center, an algae mesh surrounding the light core, and a circular water flow between the light core and the algae mesh. In such a design, the light core in the center prevents the design from being scaled up to large sizes because most of the space in the center of the bioreactor would be wasted. On the other hand, having multiple small light cores will complicate the structure of the bioreactor and increase its cost significantly.

BRIEF SUMMARY

The present invention relates to a cost-effective method for providing light deep into a liquid used in applications such as the cultivation of both attached and suspended photosynthetic organisms. The method primarily involves injecting a stream of bubbles into the liquid and a light source that shines light through the bubbles. The bubbles allow some light to travel deep into the liquid along the length of the bubble stream and also scatter/deflect some light out of the bubble stream and into the surrounding liquid. The light source can be positioned outside of the liquid and preferably has a narrow beam angle to concentrate light into the bubble stream.

There may be multiple streams of bubbles with multiple light sources in a setup. The bubbles can also be dispersed throughout the volume of the liquid to allow light to penetrate the liquid in different directions at different angles. The light sources can be positioned above, below, inside, or on the side of the body of the liquid or of the container of the liquid.

In some embodiments of the inventions, there might be a layer of transparent material that separates the light source from the liquid. For example, the light source can have a waterproof transparent housing to protect the light source when it's positioned near or submerged in the liquid. In such cases, the light source should provide light with an intensity high enough to substantially prevent growth of algae on the contact surface between the transparent material and the liquid.

Bubbles may be injected into the liquid with an air-pump and optionally an air-stone. Bubbles may also be injected using the venturi effect on a water flow within the liquid or into and out of the container of the liquid. The venturi effect can be exerted in a low/negative pressure area (e.g., before the intake of a water skimmer pump) or in a high/positive pressure area (e.g., after the outtake of a water pump).

The amount of air injected to generate bubbles in the liquid may be configured to vary over time in order to control how deep light can penetrate the liquid at different times.

BRIEF DESCRIPTION OF THE DRAWINGS

So that features of the present invention can be understood, a number of drawings are described below. It is to be noted, however, that the appended drawings illustrate only particular embodiments of the invention and are therefore not to be considered limiting of its scope, for the invention may encompass other equally effective embodiments.

DETAILED DESCRIPTION

The present disclosure provides systems and methods to employ biological organisms such as algae to filter water. Such systems and method may be used to filter, for example, freshwater and saltwater aquariums, ponds, and effluent from agricultural, human, animal and industrial sources. Filtering refers to the algae's ability to adhere to and/or filter water by physical methods and also refer to the algae's ability to consume undesirable chemicals in the water such as nitrate, phosphate, nitrite, ammonia, ammonium and even metals such as copper.

Certain example embodiments relate to a system for growing algae. The system may include a container, a plurality of meshes for growing algae disposed at a distance from each other, a light source directing light into the container, a pressurizing mechanism to push a portion of the water inside the container to create an entrainment effect creating a generally circular or spiral flow of water inside the container and over surface of the meshes, and an air source configured to introduce bubbles into the water inside of the container. The meshes may be meant for algae to grow on. For example, the surfaces of the meshes may be further coated, embedded, textured or perforated for algae growth. The light source may be configured to direct light to bubbles provided adjacent to the surfaces of the meshes for the bubbles to scatter the light to the surfaces of the meshes.

The systems and methods of this disclosure provide for a filtration system that efficiently removes undesired nutrients and/or chemicals from water without requiring additional chemicals to perform the filtration. Additional chemicals are often used to convert undesired nutrients and/or chemicals to a less undesirable form or to precipitate undesirable chemicals from solution (i.e., water). The embodiments of this application provide for systems that are quiet and reduce, and in some cases eliminate, moving parts. Embodiments of this application also provide for a compact filtration system that is not restricted to the locations where it can be placed.

The systems and methods of this disclosure is designed to eliminate and/or supplement the use of additional physical and/or chemical methods for filtration and removal of undesirable nutrients and/or chemicals. When the systems and methods of this disclosure is working in conjunction with other filtration methods, it can work in parallel or in series, or both. Working in series refers to using the systems and methods of this disclosure as a pretreatment process, or a posttreatment process for conventional physical/chemical/biological filtration processes.

Other objectives and advantages of the present invention will become apparent to the reader and it is intended that these objectives and advantages are within the scope of the present disclosure.

Figure 1A:
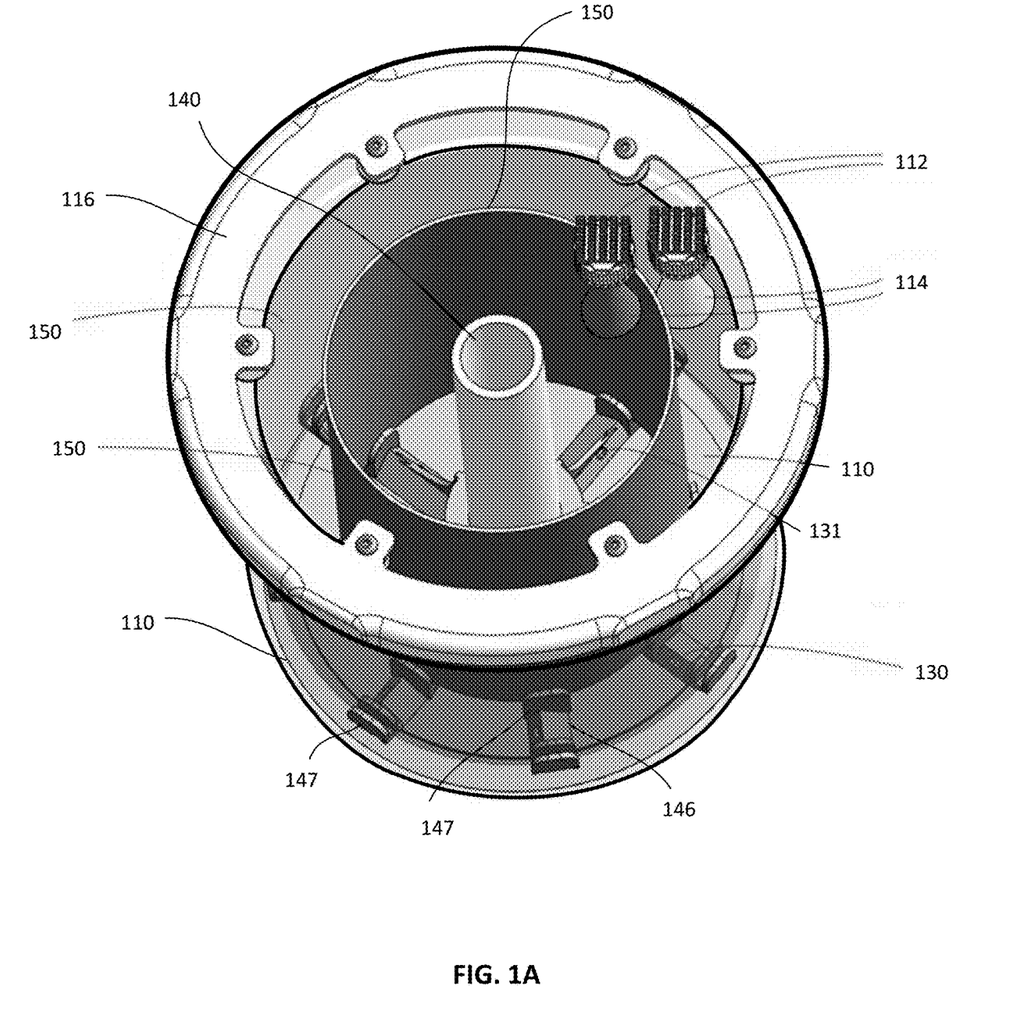
FIG. 1A illustrates a top down view of a filter system for growing algae according to an embodiment of this disclosure.
Figure 1B:
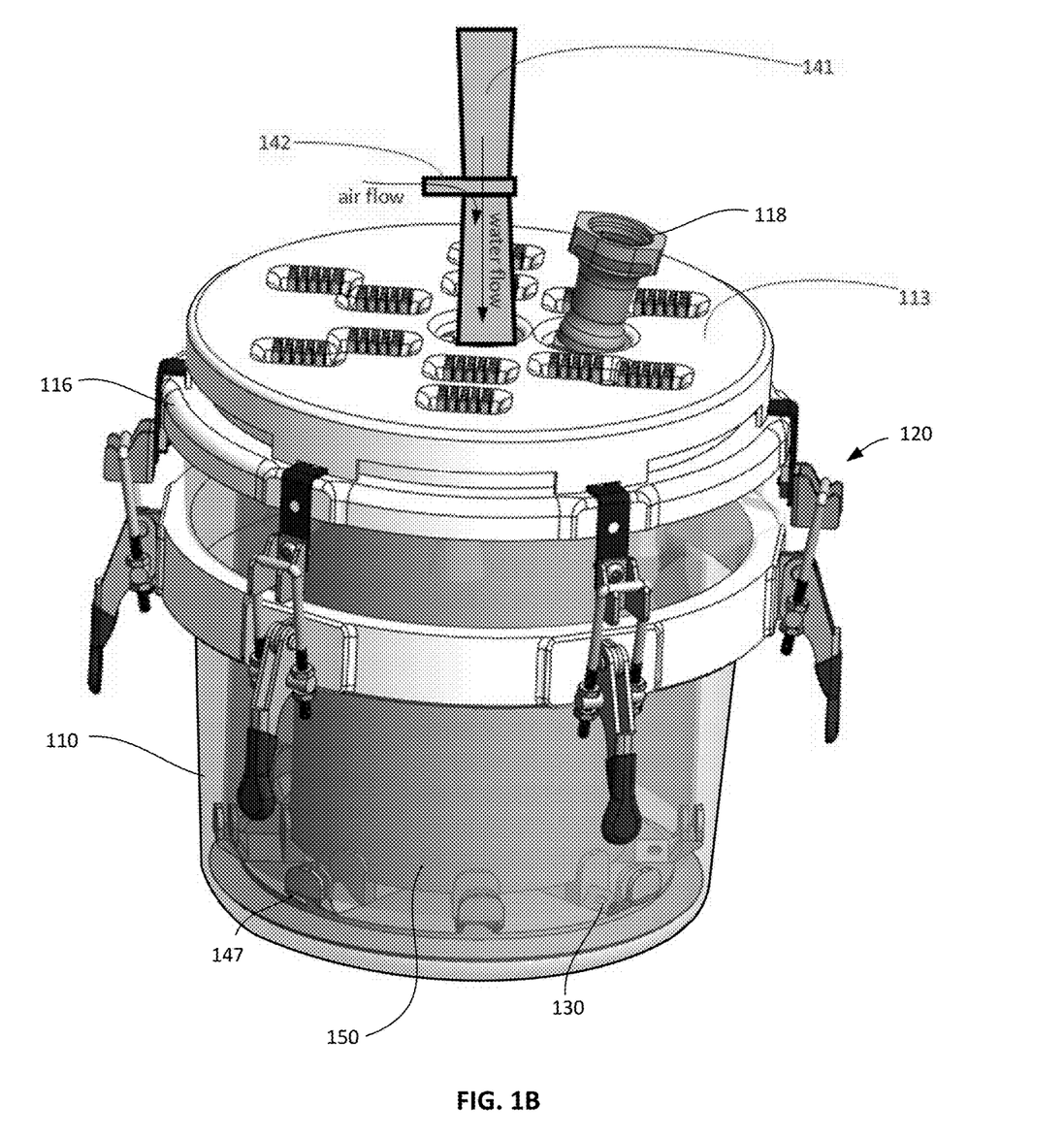
FIG. 1B illustrates a side view of the filter system illustrated in FIG. 1A for growing algae according to an embodiment of this disclosure.
Figure 1C:
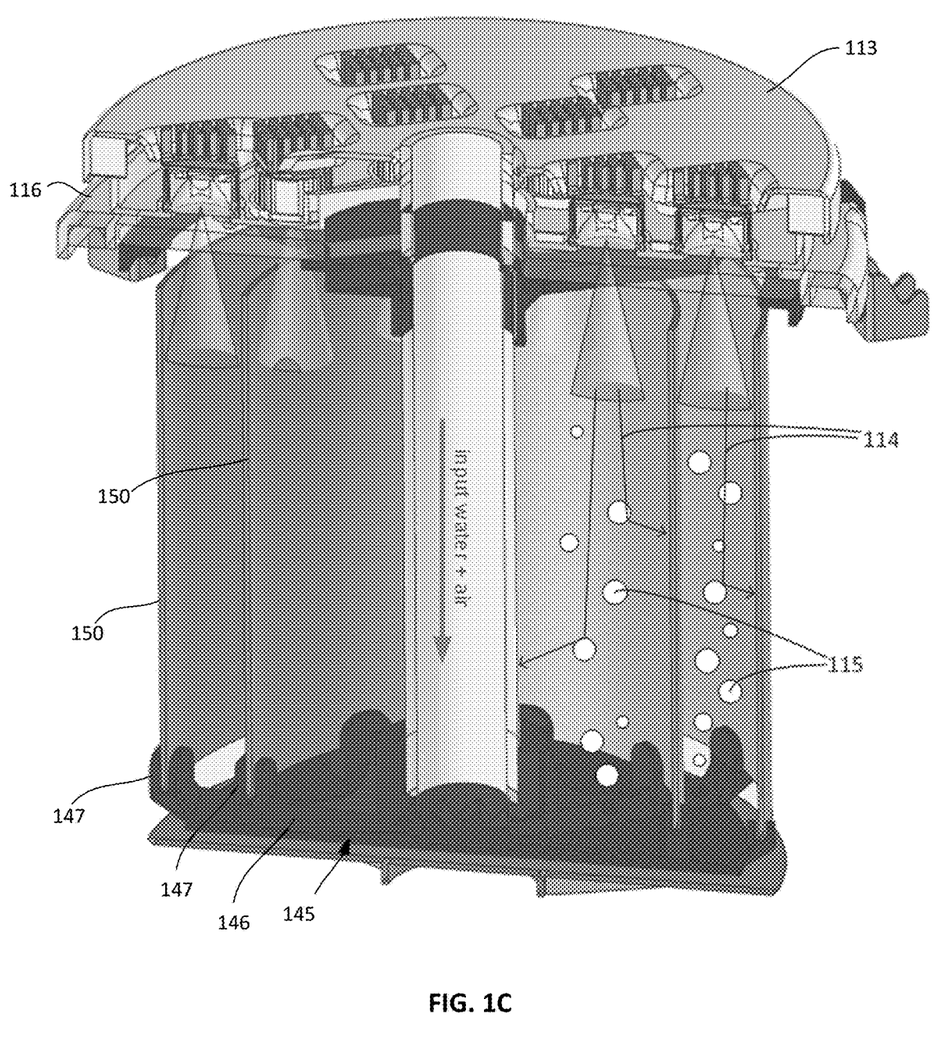
FIG. 1C illustrates a cross sectional view of the filter system illustrated in FIG. 1A for growing algae according to an embodiment of this disclosure.

FIGS. 1A-1C show a filter system for growing algae according to an embodiment of this disclosure. FIG. 1A illustrates a top down view of the filter system, FIG. 1B illustrates a side view of the filter system, and FIG. 1C illustrates a cross sectional view of the filter system. The filter system may include a container 110, a lid 116, an inlet pipe 140, a venture injector 141, a diffuser 145, and a light array 112.

The container 110 may comprise a cylindrical container having an opening on one end. The opening of the container 110 may be covered with the lid 116 secured to the container using fastening portions 120 provided in the lid 116 and/or the top portion of the container 110. In one example, the fastening portion 120 may include clips provided on the lid 116 and the container 110 to couple the lid 116 to the container 110. The container 110 may be a transparent cylindrical container. In example, only the bottom surface of the container 110 may be made of a transparent material. The container 110 may be made of plastic (e.g., acrylic) or glass. In one embodiment, the side wall and bottom of the container 110 may be non-transparent while at least a portion of the lid 116 is transparent to allow light from the light array 112 to enter the container. In one embodiment, portions of the container 110 may be coated or made of a material that does not allow for light to enter the container 110 from the sides and/or the bottom.

As shown in FIGS. 1A-1C a light assembly may be provided above at least a portion of the lid 116. The light assembly 112 is configured to provide light that is directed inside of the container 110. The light assembly 112 may be one or more of LEDs, florescent bulbs, and/or halogen bulbs, but are not so limited. The light assembly 112 may be configured to provide light with a specific spectrum that promotes algae growth inside of the container. In one embodiment, the spectrum of the light source can be adjustable to allow the user to select the desired type of light to be provided. In one embodiment, light assembly 112 may be LED strip lighting arranged in a spiral configuration on the surface of the lid 116. In some embodiments, the light assembly 112 may include heat sinks to disperse heat from the light source away from the lid 116 and water inside of the container 110.

As shown in FIGS. 1A and 1C, the lid 116 may include a transparent material (e.g., acrylic or glass) to allow light from the light assembly 112, disposed on or above a portion of the lid 116, to be provided inside the container 110. The light assembly 112 may be provided in a housing 113. In one example, the housing 113 may be removably coupled to the lid 116 and provide mounting surfaces for the light assembly 112. The housing 113 may include openings in a top surface to allow for heat sinks of the light assembly 112 to be at least partially exposed to air outside of the housing 113. As shown in FIG. 1C, the lights may be coupled to the housing 113 and disposed between the lid 116 and the housing 113. In some embodiments, the light assemblies may be coupled to the lid 116 without having a housing 113.

The venture injector 141 may be configured to receive water and/or air from outside of the container 110 via the inlet pipe 140 and disperse the water and/or air inside of the container 110 via a diffuser 145 (e.g., near the bottom of the container 110). The water and/or air from inside the container 110 may exit via an outlet 118 provided in the lid 116. In some example, the outlet 118 may be provided in other locations of the system such as a top portion of the container 110. In some example, the lid 116 may include an exhaust assembly to remove air from inside of the container 110.

The venture injector 141 may have an inlet for receiving water and an air inlet 142 for receiving air. The venture injector 141 is configured to mix the water and air. The air inlet 142 may include an integrated one-way check valve to prevent water from going out via the air inlet 142 (e.g., when the air supply is turned off or air supply pressure is reduced). The mixture of water and air form the venture injector 141 is provided to an inlet pipe configured directs the water and air from the top of the container to the diffuser 145 disposed in a bottom surface of the container 110. As shown in FIGS. 1B and 1C, the diffuser 145 may include a plurality of outlets 130 and/or 131. The outlets 130 and 131 are arranged in a circular pattern at different distances from the center of the container 110. The outlets 130 and/or 131 may be configured to direct water flow in directions that are perpendicular to the bottom surface of the container 110 or directions that are angled relative to the bottom surface of the container 110.

The diffuser 145 may include a plurality of ribs 146 coupled to and extending in radial directions from the inlet pipe. A plurality of outlets 130 and 131 may be provided along each of the ribs 146. Water and air from the inlet tube may travel inside the ribs 146 and exit into the container 110 via the outlets 130 and 131. Water and air exiting the outlets 130 and 131 may be pressurized and create an entrainment effect providing a generally circular or spiral flow of water inside the container 110.

The ribs 146 may include inserts 147 for receiving one or more surfaces 150 on which algae will grow. The surfaces 150 may be removable for cleaning and/or replacement. Each rib 146 may include an insert 147 provided at a same distance from the center of the container 110. In one example, each rib 146 may include a plurality of inserts 147 provided at different radial distances from the center of the container 110. In one example, the lid 116 may include similar inserts configured to hold the surfaces 150 in place at an opposite end of the surface from the end disposed at the bottom surface of the container 110.

The surface 150 may be made of a material (e.g., plastic) that facilitates growth of algae. The surface 150 may be permeable for nitrifying and photosynthesizing algae. In one embodiment, the surface 150 may be a flexible mesh and/or resilient mesh to allow the surface 150 to conform to the surface of the container 110. The surface 150 may be provided with a specific texture that is designed to promote algae growth. The surface 150 may also be a cloth with micro-/nano-fiber to provide a rough surface to facilitate algae cells' attachment. The cloth may be sewed to a plastic mesh. In one embodiment, the surface 150 may be provided with application of live algae to expedite growth of the algae during initial installation of the system.

The inserts 147 may be configured to hold surfaces 150 such that they are provided parallel to each, parallel to an inside surface of the container 110, and/or parallel to a surface of the inlet pipe. The inserts 147 may be configured to hold the surfaces 150 at predetermined distances from the inside surface of the container 110 and/or other surfaces 150. As shown in FIGS. 1A and 1C, the surfaces 150 may be disposed inside of the container such that the light assemblies 112 directs light between the surfaces 150, between the inside surface of the container and the surface 150, and/or between the inlet pipe and the surface 150. Similarly, the outlets 130 and 131 may be provided between the surfaces 150, between the inside surface of the container and the surface 150, and/or between the inlet pipe and the surface 150. In this manner light and the flow of water and air mixture is provide to both sides of the surface 150. This configuration encourages more even distribution of light and water/air to the surfaces 150 and provides for better algae growth. This configuration allows for the entrainment effect providing a generally circular or spiral flow of water to be provided between the surfaces 150, between the inside surface of the container and the surface 150, and/or between the inlet pipe and the surface 150.

As shown in FIG. 1C, light 114 from the light assemblies is directed in a downward direction and the water flow with the bubbles 115 travels in an upward direction. Accordingly, the light 114 and the bubbles 115 travel in different directions and light 114 is scattered and/or deflected by the bubbles 115 at different depths of the container. In this manner, the light reaches not just different depths of the container but is also directed toward the sides of the surface 150 at different depths of the container 110 due to the light being scattered and/or deflected by the bubbles 115 at different depths.

In some embodiments, the systems described in commonly-assigned U.S. patent application Ser. No. 15/546,176, title "ALGAE SCRUBBER WITH DIRECTED WATER FLOW," filed Jul. 25, 2017, (patent application WO2016123077 A1) may be modified to utilize one or more embodiments of the lighting method described in this application. For example, the system described in FIG. 7 of U.S. patent application Ser. No. 15/546,176 may be configured to utilize one or more aspects of the invention as disclosed in FIGS. 1A-1C of this document. A portion 111 of the lid 116 may be made of a transparent material like acrylic or glass. A light assembly 112 (e.g., LEDs+heatsinks) may be positioned on top of the lid and configured to shine light down into the container through the transparent portion 111 of the lid. The light assembly may be put in a housing 113. With this configuration, the light core in the original design disclosed in the patent application WO2016123077 A1 may be removed. Additional algae screens 150 can be put in the container and positioned vertically in parallel with a first algae screen 150 with some space between them. This configuration allows utilization of most of the volume of the filter/container to provide additional surface area for growing algae. As discussed above, the diffuser 145 may have outlets 131 in addition to the original outlets 130 to create additional circular/spiral flows over the additional grow surfaces. A venturi injector 141 may be connected to the water inlet on the lid of the filter to mix air from the air valve 142 (that has an integrated one-way check valve) with the water flowing into the filter. As air and water exit the outlets of the diffuser 145, bubbles 115 will be dispersed throughout the volume of the filter. Light 114 with a narrow beam angle coming down from the light sources on the top will be scattered/deflected by the bubbles 115 to the sides and onto the algae screens.

The amount of air going into the venturi injector 141 may be controlled to vary over time. For example, an air pump may be connected to the air valve of the venturi injector and the air pump can be turned on and off periodically automatically via an electronic control system. This will allow light to penetrate the water at different depths at different times before being deflected/scattered by the bubbles to the sides. In some examples, the light and air going into the venturi injection 141 may be turned on and off together.

Figure 2:
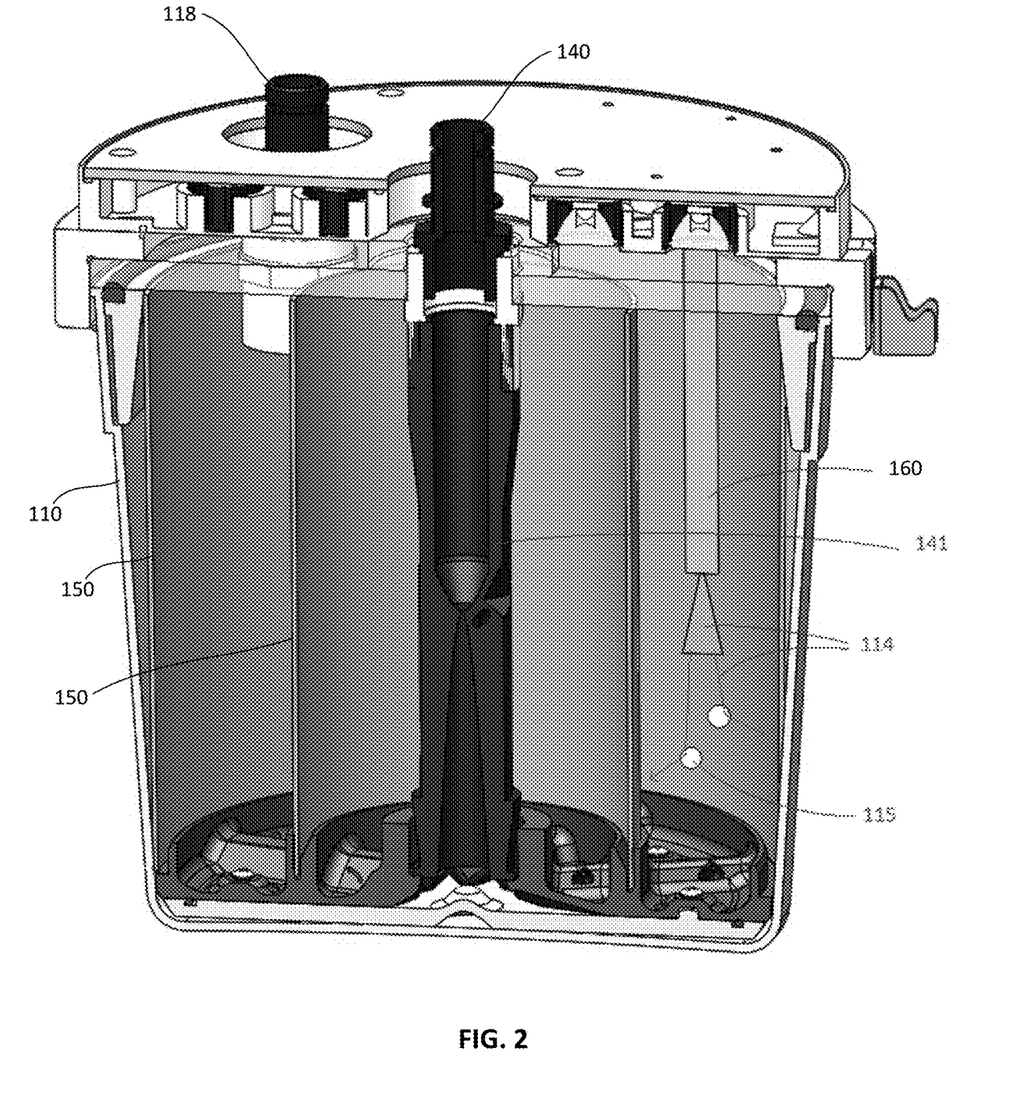
FIG. 2 illustrates a filter system for growing algae according to another embodiment of this disclosure.

FIG. 2 illustrates a filter system for growing algae according to another embodiment of this disclosure. FIG. 2 shows a cross sectional view of a filter system including a light conductor 160. The light conductor 160 (e.g., a fiber optic cable) can be used to conduct light from a light source to a point deep inside the liquid body. Light 114 from a light source may travel via the light conductor 160, escape at the end of the light conductor 160 deep inside the liquid body, and be scattered/deflected by the bubbles 115 to the surrounding to promote algae growth. In some embodiments, a portion of light from a same light source may be provided directly from the light source to one portion of the container 110 (e.g., a top portion) and another portion of the light may be provided to another portion of the container 110 (e.g., a bottom portion) via the light conductor 160.

In some examples, the light conductor 160 may be coupled to the lid 116 and/or the light source (e.g., light assembly 112 shown in FIG. 1A). As shown in FIG. 2, the light conductor is disposed between two surfaces 150. While not illustrated in FIG. 2, another light conductor may be provided between the inlet pipe 140 and the surface 150 closest to the inlet pipe.

Figure 3:
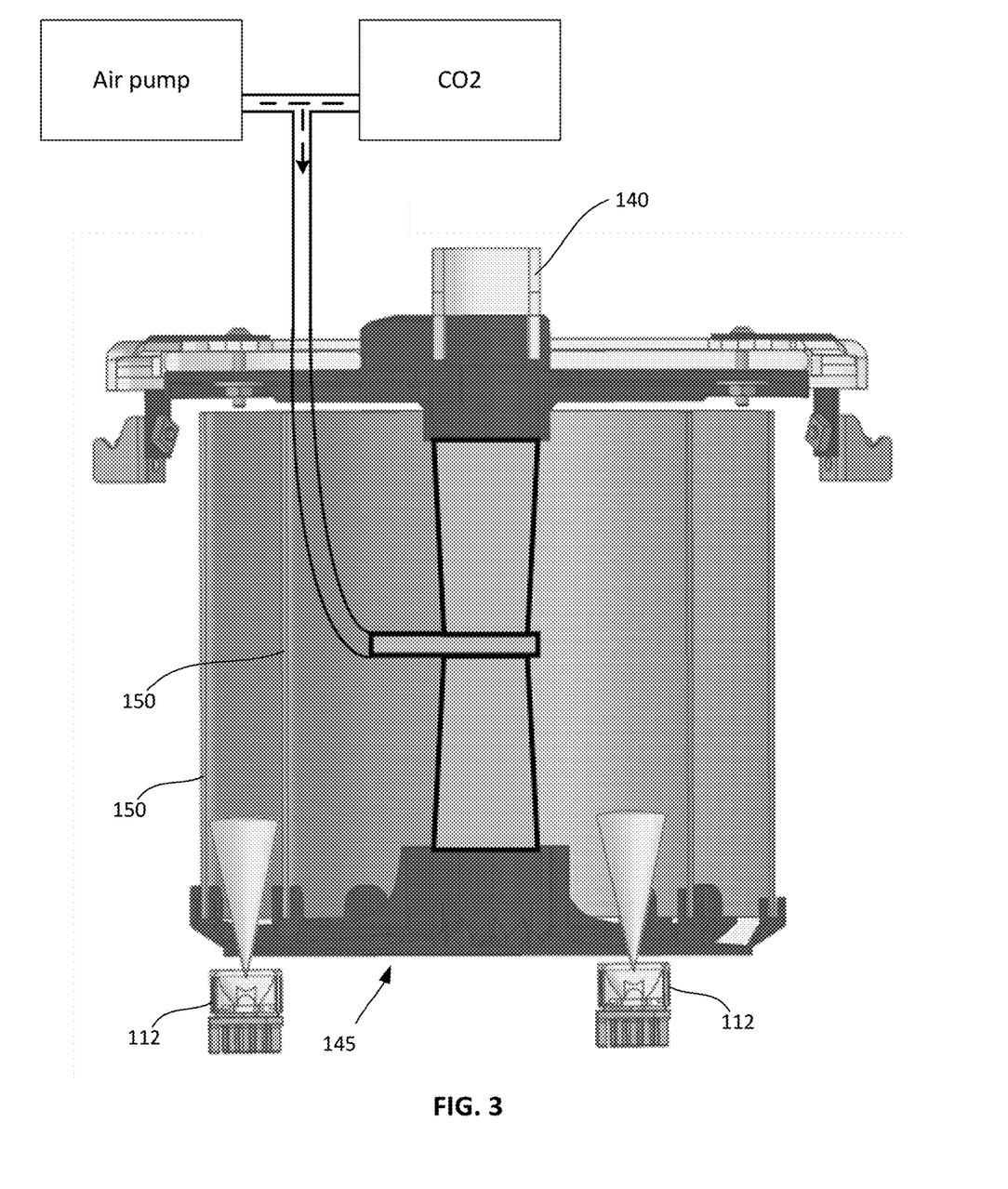
FIG. 3 illustrates a filter system for growing algae according to another embodiment of this disclosure.

FIG. 3 illustrates a filter system for growing algae according to another embodiment of this disclosure. FIG. 3 show a cross sectional view of a filter system including a light source 112 positioned at the bottom of a container 110. A portion of the bottom of the container 110 may be transparent to allow for light to travel inside of the container 110 from the light source 112. Then, the light source 112 may be configured to shine light up into the container through the transparent portion of the container 110. In the example, shown in FIG. 3, the direction of the light and the flow of water and bubbles in the same direction. The configuration of the light source shown in FIG. 3 may be used together with the light source configuration shown in FIGS. 1A-1C.

As shown in FIGS. 2 and 3, the venturi injector 141 may be made as part of the input water pipe 140 inside the filter and the air valve can be connected to a hose going through the lid. In case the input water flow is not strong enough to pull air in, an external air pump can be connected to the air valve of the venturi injector 141 to help push air in. Carbon dioxide (CO2) may also be mixed in with the air going into the filter to accelerate the growing of algae.

As shown in FIGS. 1B, 2, and 3, the venturi injector 141 may include an inlet for receiving water and an outlet, which are approximately the same size as the inlet, for outputting a mixture of water and air. The diameter of the venturi injector 141 may decrease along the body from the inlet to a portion of the venturi injector 141 where air and/or CO2 is introduced into the water. The diameter of the venturi injector 141 may increase along the body from where air and/or CO2 is introduced into the water to the outlet of the venturi injector 141. This configuration provides better introduction of bubbles to the water by changing pressure of the water at a point where the air and/or CO2 is introduced into the water. In the venturi effect, the pressure of a gas may be reduced just beyond an obstruction or restriction in the vessel through which the gas is flowing (see e.g., www-.medical-dictionary.thefreedictionary.com/Venturi+effect). The pressure drop can be nearly eliminated if dilation of the vessel does not exceed 15 degrees.

Figure 4:
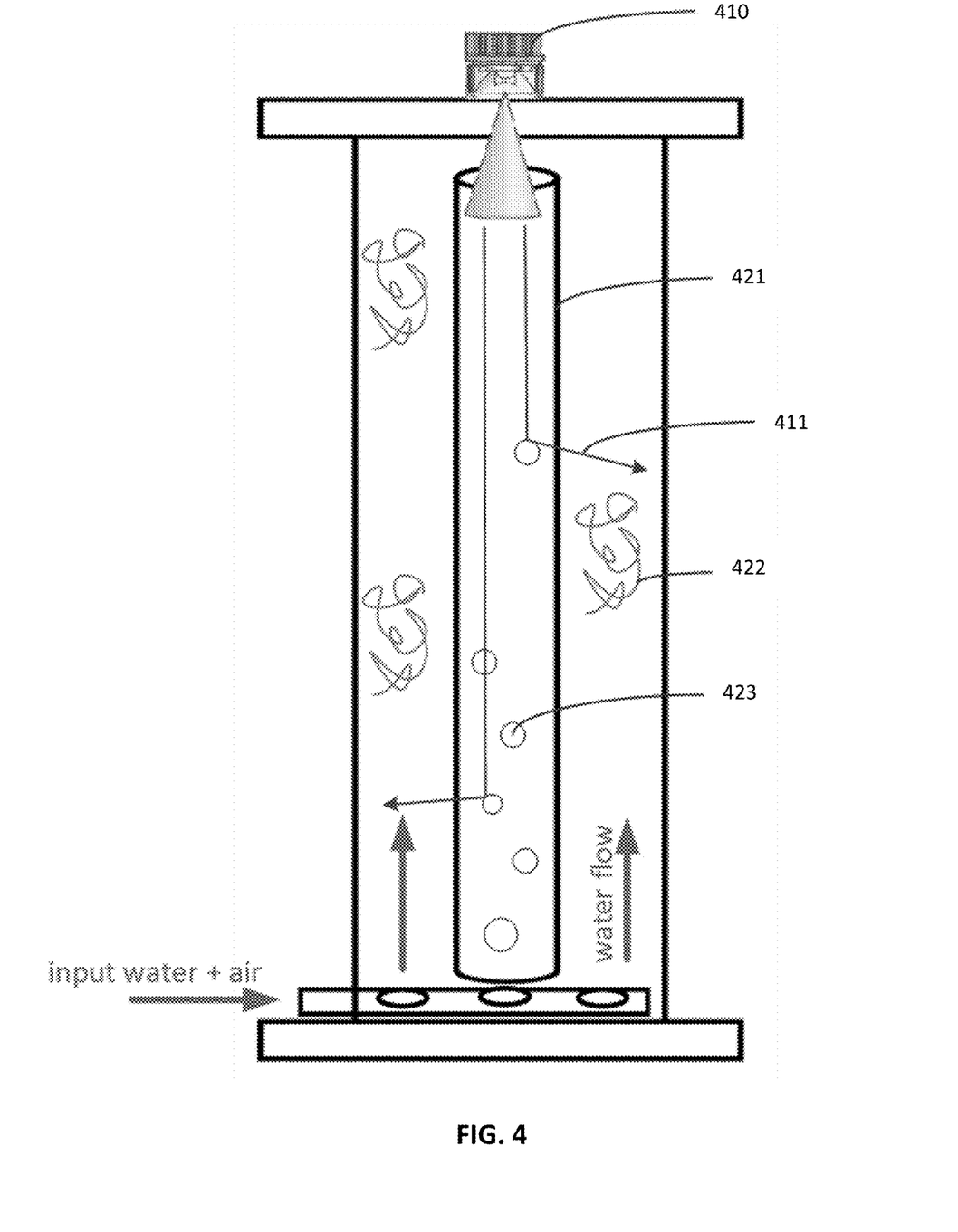
FIG. 4 illustrates a macroalgae reactor according to an embodiment of this disclosure.

The In some embodiments, the system described in FIGS. 1, 2, and/or 3 in the U.S. Pat. No. 9,388,372 (which is hereby incorporated by reference) may be modified to utilize the lighting method(s) described in this application. FIG. 4 illustrates a macroalgae reactor according to an embodiment of this disclosure. FIG. 4 illustrates aspect of the disclosed embodiments shown in FIG. 3, in combination with a system disclosed in U.S. Pat. No. 9,388,372. The light source 410 may be positioned on the top of the container shining light 411 down the transparent tube 421. Air may be injected into the input water to generate bubbles 423 floating up the tube 421. Alternatively, bubbles may be generated by a separate air pump connected to an air stone placed at the bottom of the tube 421. Light 411 from the light source 410 will be deflected/scattered by the bubbles 423 to the side and onto the algae 422 (e.g., macroalgae).

Figure 5:
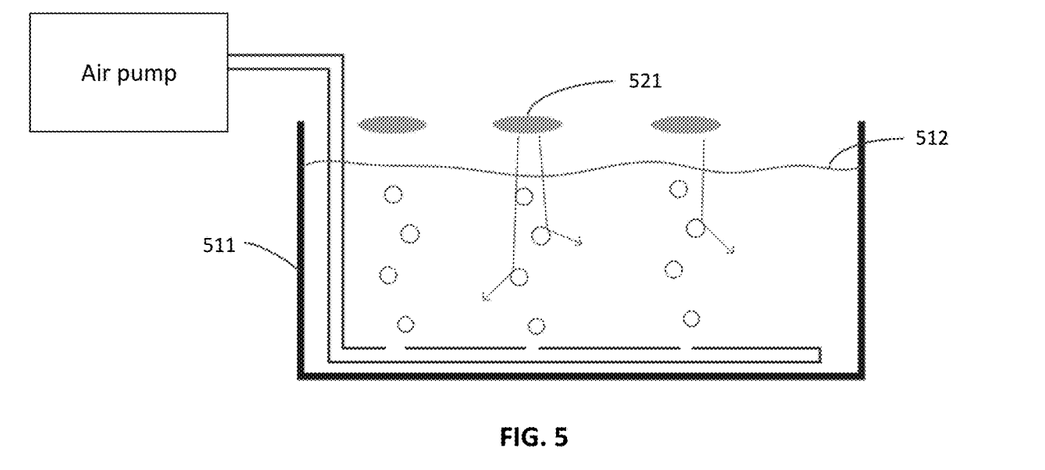
FIG. 5 illustrates an open pond system for growing algae according to an embodiment of this disclosure.

FIG. 5 illustrates an open pond system for growing algae according to an embodiment of this disclosure. FIG. 5 shows how the lighting method(s) disclosed in this application can be utilized in open pond systems. Bubbles may be injected at various points on the bottom of the pond 511. Optical lens 521 may be positioned above the water line 512 to focus sunlight into narrow light beams on top of the bubble columns. As bubbles float up, they will allow light from above to penetrate deep into the pond and reach the algae around the bubble columns. In some examples, the optical lens 521 may be configured to flow at the water line 512.

Figure 6:
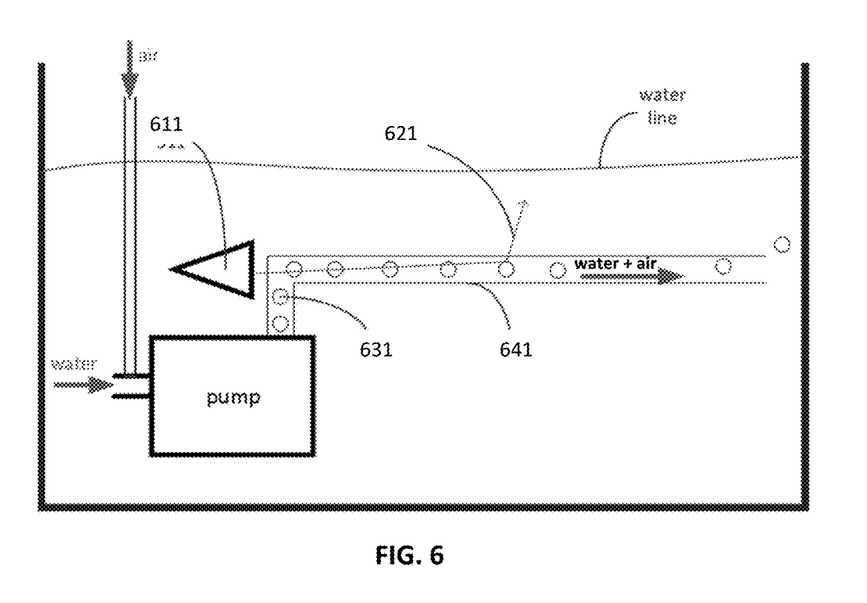
FIG. 6 illustrates a system including a horizontal bubble pipe for growing algae according to another embodiment of this disclosure.

FIG. 6 illustrates a system including a horizontal bubble pipe for growing algae according to another embodiment of this disclosure. As shown in FIG. 6, in some embodiments, bubbles can be injected and pushed through a transparent horizonal pipe 641 going through a liquid in a container to provide light to areas surrounding the pipe. A submersible pump may be configured to mix air and water at the intake and push them through the transparent pipe 641. A light source 611 may be configured to shine light through the transparent pipe 641 from one of its ends. Light 621 from the light source 611 will travel inside and along the transparent pipe 641 and will be deflected/scattered by the bubbles 631 into the water surrounding the pipe 641. The light intensity from the light source 611 should be high enough to prevent algae from growing on the walls of the transparent pipe. The pipe 641 may have any suitable shape that facilitates light travelling inside and along its length.

Figure 7:
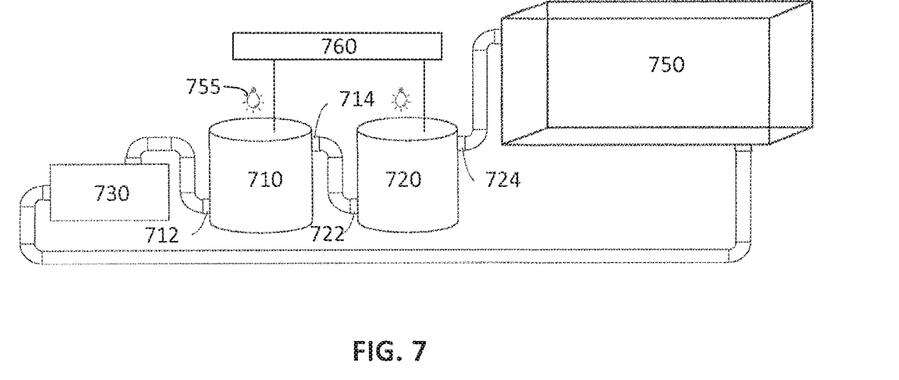
FIG. 7 illustrates a filter system including a plurality of filters according to an embodiment of this disclosure.

FIG. 7 illustrates a filter system including a plurality of filters according to an embodiment of this disclosure. The filter system may include a first algae filter 710 that is connected in series to a second algae filter 720. The first algae filter and/or the second algae filter may include one or more features of filters disclosed in this application. A pressurized mechanic 730 may pump water from a water tank (e.g., an aquarium or a pond) 750 and supply the water to an inlet 712 in the first algae filter 710. The pressure created by the pressurized mechanism 730 may move the water inside of the first algae filter 710 and outside of the first algae filter 710 via the outlet 714. The outlet 714 of the first algae filter 710 may be coupled to an inlet 722 of the second algae filter 720 to provide the water from the first algae filter 710 to the second algae filter 720. The pressure created by the pressurized mechanism 730 may move the water inside of the second algae filter 720 and outside of the second algae filter 720 via the outlet 724. The outlet 724 of the second algae filter 720 may be coupled to the water tank 750 to supply water filtered by the first and second algae filters 710 and 720 to the water tank 750.

An air supply 760 may be configured to supply air into the first and/or second filters to create a stream of bubbles inside of the filters so that light from one or more light sources 755 can be dispersed more evenly to the algae screens inside of the filters.

The air and water tight lids provided in the first and second algae filters may allow for pressure generated by a single pressurized mechanic 730 to move water in both of the filters. In addition, the air and water tight lids may allow for the filters to be positioned at any location, even at locations that are higher than the water tank 750.

The filter system shown in FIG. 7 is not limited to the first and second algae filters 710 and 720. But may include a single algae filter or a plurality of algae filters connected in daisy-chain and/or in parallel. In one embodiment, a separate pressurized mechanic 730 may be provided for each algae filter.

Figure 8:
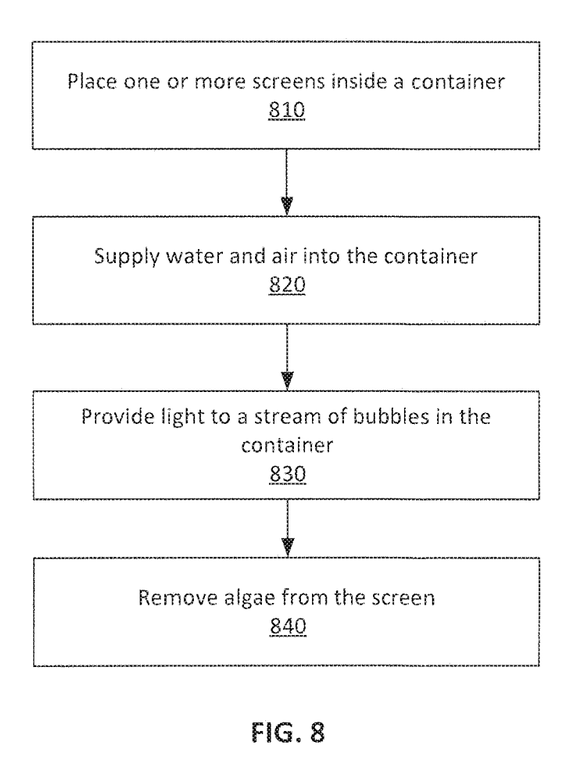
FIG. 8 illustrates a method of growing algae in a filtration system according to an embodiment of this disclosure.

FIG. 8 illustrates a method of growing algae in a filtration system according to an embodiment of this disclosure. The method may include placing one or more screens inside of a container 810, supplying water and air inside of the container 820, providing light to a stream of bubbles in the container 830, and removing algae from the surface of the one or more screens 840.

The one or more screens may be placed inside of a cylindrical container such that the surfaces of the screen is provided at a distance from each other and/or the side surface of the container. The screen(s) may be secured via grooves provided on the bottom surface of the cylindrical container or via a screen retainer that secures the screens on the edges of the screen at the bottom of the container and/or at the top of the container. The screen(s) may be secured via inserts 147 discussed with reference to FIGS. 1A-1C. The screen(s) may be provided such that at least some portions of the screens overlap.

The water may be supplied inside of the container via a pump provided inside or outside of the container. The pump may push a portion of the water inside the container to create an entrainment effect providing a generally circular or spiral flow of water inside the container and over the surface of the screen(s). Outlets to push the water inside of the container may be provided between the screens, a screen and an inlet pipe in the center of the container, and/or a screen and the side of the container to create the generally circular or spiral flow of water along each surface of the screens. An air source may be configured to introduce air into the water so that a flow of bubbles is created in the flow of water between the screens, a screen and an inlet pipe in the center of the container, and/or a screen and the side of the container. The air source may include a pump and/or CO2 source.

The light source may be provided inside and/or outside of the container to provide light into the container. The light source may be directed towards the bubbles generated next to the surface of the screens so that the bubbles may scatter and/or deflect the light from the light to the surfaces of the screens. In some embodiments, the light source may be provided on the bottom and/or the top of the container including a transparent surface. The light source and/or the air supply may be set to periodically turn off and on manually or automatically via a timer to optimize the algae growth. The time may be implemented via a processing system including a processor. In some examples, the light source and/or the air supply may be controlled to turn on and off together.

The presence of light and flow of water with bubbles will encourage algae to grow on all surface of the screen and depths in the container. As the screen gets filled up with algae, the algae may be removed from surface of the screen to allow for more algae to grow. Removing the algae may prevent old algae from dying because the old algae does not receive sufficient light from the light source.

While the various embodiments discussed above utilize growing algae on a surface, other plants and photo synthesizing organisms may be encouraged to grow on the surface to filter the water. In some embodiments, the screen may be seeded with the algae. In some embodiment, genetically engineered algae that is designed to enhance the filtration of the water may be provided on the screen.

Reference in the specification to "one embodiment" or "an embodiment" means that a particular feature, structure, or characteristic described in connection with the embodiment may be included in at least an implementation. The appearances of the phrase "in one embodiment" in various places in the specification may or may not be all referring to the same embodiment. In addition, some part/components discussed above may be combined and/or separated to provide the same and/or different parts. For example, one or more parts/components may be provided as a single part by manufacturing a single part (e.g., by 3D printing).

Also, in the description and claims, the terms "coupled" and "connected," along with their derivatives, may be used. In some embodiments of the invention, "connected" may be used to indicate that two or more elements are in direct physical contact with each other. "Coupled" may mean that two or more elements are in direct physical contact. However, "coupled" may also mean that two or more elements may not be in direct contact with each other, but may still cooperate or interact with each other.

Thus, although embodiments of the invention have been described in language specific to structural features and/or methodological acts, it is to be understood that claimed subject matter may not be limited to the specific features or acts described. Rather, the specific features and acts are disclosed as sample forms of implementing the claimed subject matter.

In the above description, numerous specific details are set forth to provide a thorough understanding of embodiments of the invention. The invention is capable of other embodiments and of being practiced and carried out in various ways. One skilled in the relevant art will recognize, however, that the invention can be practiced without one or more of the specific details or with other methods, components, techniques, etc. In other instances, well-known operations or structures are not shown or described in details to avoid obscuring aspects of the invention. Also, it is to be understood that the phraseology and terminology employed herein are for the purpose of the description and should not be regarded as limited.

Although the processes illustrated and described herein include series of steps, it will be appreciated that the different embodiments of the present invention are not limited by the illustrated ordering of steps, as some steps may occur in different orders, some concurrently with other steps apart from that shown and described herein. In addition, not all illustrated steps may be required to implement a methodology in accordance with the present invention. Moreover, it will be appreciated that the processes may be implemented in association with the apparatus and systems illustrated and described herein as well as in association with other systems not illustrated.

I claim:

1. A method for providing light deep into liquid disposed inside of a container, the container including a water inlet, a water outlet, and a water-tight lid configured to enclose the container, the method comprising:

using a light conductor, at least partly submerged in the liquid, to conduct a narrow-angled light beam from a light source disposed outside of the liquid to a point inside the liquid inside the container, the light beam having an intensity high enough to prevent growth of algae on a surface of the light conductor inside the liquid where the light beam escapes the light conductor; and injecting a stream of bubbles into the liquid wherein the stream of bubbles intersects and scatters or diffuses the narrow-angled light beam escaping from the surface of the light conductor.

2. The method of claim 1, wherein the bubbles are injected into the liquid using an air pump or an air stone connected to the air pump.

3. The method of claim 1, wherein the bubbles are injected into the liquid using a venturi effect.

4. The method of claim 3, wherein the venturi effect is created by connecting an airline to a water line, wherein
the water line has water coming into the liquid; and
the airline is connected to an area of low pressure of the water line.

5. A system for growing macroalgae or microalgae attached to a mesh surface or suspended in a liquid, the system comprising:
the container for the liquid in which algae is to be cultured; and
the method of claim 1 to provide light into the liquid and onto the algae submerged in the liquid.

6. The system of claim 5 for growing attached microalgae, wherein the light is deflected and/or scattered by the bubbles onto a surface inside the container on which algae is to be grown.

7. The system of claim 5, wherein
the bubbles are pushed through a transparent water pipe a portion of which is submerged in the liquid; and
the light is shined through the submerged portion of the pipe.

8. The system of claim 7 for growing microalgae, wherein
a transparent tube is disposed vertically inside the container;
the light comes from a light source positioned on top of the container and comes down into the tube; and
the bubbles are injected into the tube at a bottom surface of the container.

9. The system of claim 5 for growing suspended microalgae in the container wherein the bubbles are injected at one or more points on a bottom surface of the container.

10. The method of claim 1, wherein an amount of air/bubbles injected into the liquid is varied over time.

11. A system for growing algae using the method of claim 1.

12. The method of claim 1 wherein the light source is positioned above a first surface of the lid and is configured to provide light to the light conductor coupled to a second surface of the lid opposite to the first surface.

13. A water filtering system for growing algae, the system comprising:
a container having a cylindrical inner surface and an opening at one end of the container;
a water-tight lid configured to cover the opening of the container, wherein a portion of the lid is transparent and a portion of the lid is non-transparent;
a plurality of screens disposed inside the container such that surfaces of the plurality screens are parallel to each other and to the cylindrical inner surface of the container;
a diffuser disposed near a bottom surface of the container;
a venturi injector configured to receive water from outside of the container, mix the water with an air source, and provide the water and air mixture to the diffuser, wherein the diffuser is configured to disperse the water and air mixture via a plurality of outlets disposed at different locations near the bottom surface of the container and between the parallel surfaces of the plurality of screens;
a plurality of light conductors disposed inside of the container adjacent to the transparent portion of the lid and at least partly submerged in the water; and
a plurality of light sources disposed outside of the container on a surface of the lid and configured to direct narrow-angled light beams to the plurality of light conductors through the transparent portion of the lid, wherein the light conductors are configured to direct the received light towards streams of bubbles in the water and air mixture, wherein the streams of bubbles intersect and scatter or diffuse the narrow-angled light beams and the light beams have an intensity high enough to prevent growth of algae on surfaces of the light conductors where the beams of light go through into the water and air mixture.

14. The water filtering system of claim 13, wherein the light sources and the air mixture are configured to be turned on and off at specified time intervals.

15. The water filtering system of claim 13, wherein at least one outlet of the diffuser is provided between adjacent screens, and at least one outlet of the diffuser is provided between the cylindrical inner surface and an adjacent screen.

16. The water filtering system of claim 15, wherein at least one light source is provided between adjacent screens, and at least one light source is provided between the cylindrical inner surface and the adjacent screen.

17. A bioremediation liquid filtering apparatus, the apparatus comprising:
a cylindrical container;
a water-tight lid configured to cover the cylindrical container and including an outlet for removing liquid and air from the cylindrical container, wherein a portion of the water-tight lid is transparent and a portion of the water-tight lid is non-transparent;
an inlet assembly disposed through the lid, configured to receive a liquid and air from outside of the cylindrical container and configured to provide a mixture of liquid and air near a bottom surface of the cylindrical container via a plurality of outlets arranged in a plurality of circles at different distances from the center of the cylindrical container;
a plurality of circular screens for growing algae, wherein the plurality of circular screens are disposed inside the cylindrical container with surfaces of the screens being parallel to each and displaced from each other and the inside surface of the cylindrical container, and the plurality of circular screens are arranged such that at least one outlet of the plurality of outlets is provided between each pair of circular screens and at least one outlet of the plurality of outlets is provided between the inside surface of the cylindrical container and an adjacent circular screen;
a plurality of light conductors dispose at least partly submerged in the mixture of liquid and air inside of the container and coupled to the inside surface of the lid adjacent to the transparent portion of the lid, wherein at least one light conductor is provided between each pair of circular screens and at least one light conductor is provided between the inside surface of the cylindrical container and the adjacent circular screen; and
a plurality of light sources disposed outside of the container and above the transparent portion of the lid and configured to direct light to the plurality of light conductors inside of the container via the transparent portion of the lid, wherein the light conductors are configured to direct the light received from the light source towards bubbles in the mixture of liquid and air between each pair of circular screens and between the inside surface of the cylindrical container and the adjacent circular screen, and the light has an intensity high enough to prevent growth of algae on surfaces of the light conductor inside of the container and liquid where the light goes through.

18. A system for growing algae, the system comprising:
a container for a liquid, the container including a water inlet, a water outlet, and a water-tight lid,
a light conductor disposed inside of the container having one end coupled to the lid and a second end disposed in a portion of the container configured to hold the liquid,
a light source positioned outside of the container and adjacent to the lid and configured to output a narrow-angled light beam to the light conductor through the lid and into the portion of the container configured to hold the liquid, the narrow-angled light beam having an intensity high enough to prevent growth of algae on a surface of the light conductor disposed in the portion of the container configured to hold the liquid and where the narrow-angled light beam goes through into the water, and
an apparatus comprising a plurality of outlets configured to inject a stream of bubbles into the portion of the container configured to hold the liquid and where the narrow-angled light beam from the surface of the light conductor enters the portion of the container configured to hold the liquid, the stream of bubbles intersecting and scattering or diffusing the narrow-angled light beam.

19. The system of claim 18, wherein the container is a cylindrical container and the system further comprises: a plurality of screens for growing algae, wherein the plurality of screens are disposed inside the cylindrical container with surfaces of the screens being parallel to each and the inside surface of the cylindrical container, the plurality of screens are displaced from each other and the inside surface of the cylindrical container, the bubbles are injected between the plurality of screens, and the light source includes a plurality of light sources, each disposed above and between the plurality of screens and configured to direct light beam between the plurality of screens.

20. The system of claim 18, wherein the lid includes an exhaust assembly configured to remove air from inside of the container.

* * * * *